(12) United States Patent
Fahey

(10) Patent No.: US 9,126,039 B2
(45) Date of Patent: Sep. 8, 2015

(54) SYNERGISTIC MUSCLE ACTIVATION DEVICE

(71) Applicant: NIVEUS MEDICAL, INC., Redwood City, CA (US)

(72) Inventor: Brian J. Fahey, Palo Alto, CA (US)

(73) Assignee: NIVEUS MEDICAL, INC., Redwood City, CA (US)

( * ) Notice: Subject to any disclaimer, the term of this patent is extended or adjusted under 35 U.S.C. 154(b) by 59 days.

(21) Appl. No.: 14/070,210

(22) Filed: Nov. 1, 2013

(65) Prior Publication Data

US 2014/0058477 A1 Feb. 27, 2014

Related U.S. Application Data

(62) Division of application No. 12/943,486, filed on Nov. 10, 2010, now Pat. No. 8,588,901.

(60) Provisional application No. 61/260,324, filed on Nov. 11, 2009.

(51) Int. Cl.
| *A61N 1/36* | (2006.01) |
| *A61N 1/04* | (2006.01) |
| *A61F 7/00* | (2006.01) |
| *A61F 7/02* | (2006.01) |

(52) U.S. Cl.
CPC .......... *A61N 1/36003* (2013.01); *A61N 1/0452* (2013.01); *A61N 1/0476* (2013.01); *A61N 1/0492* (2013.01); *A61F 2007/0054* (2013.01); *A61F 2007/0298* (2013.01); *A61N 1/0456* (2013.01); *A61N 1/36021* (2013.01)

(58) Field of Classification Search
CPC ............ A61N 1/36003; A61N 1/0452; A61N 1/0476; A61N 1/0492; A61N 1/36021; A61N 1/0456; A61F 2007/0054; A61F 2007/0298
USPC .................................. 607/2, 3, 48, 148, 152
See application file for complete search history.

(56) References Cited

U.S. PATENT DOCUMENTS

| 4,108,146 A | 8/1978 | Golden |
| 4,390,023 A | 6/1983 | Rise |
| 4,480,830 A | 11/1984 | Petrofsky et al. |
| 4,580,569 A | 4/1986 | Petrofsky |
| 4,619,266 A | 10/1986 | Hodgson |
| 4,736,752 A | 4/1988 | Munck et al. |
| 4,805,636 A | 2/1989 | Barry et al. |
| 4,811,742 A | 3/1989 | Hassel et al. |
| 4,838,272 A | 6/1989 | Lieber |

(Continued)

FOREIGN PATENT DOCUMENTS

| FR | 2596654 A | 10/1987 |
| JP | 2001-025510 | 1/2001 |

(Continued)

OTHER PUBLICATIONS

Baker et al.; Effects of waveform on comfort during neuromuscular electrical stimulation; Clin Ortho Res; vol. 233; pp. 75-85; Aug. 1988.

(Continued)

*Primary Examiner* — Amanda Patton
(74) *Attorney, Agent, or Firm* — Shay Glenn LLP

(57) ABSTRACT

Systems and methods of use for guiding the flow of energy through a subject to stimulate tissue.

18 Claims, 7 Drawing Sheets

(56) References Cited

U.S. PATENT DOCUMENTS

| | | |
|---|---|---|
| 4,867,166 A | 9/1989 | Axelgaard et al. |
| 4,962,761 A | 10/1990 | Golden |
| 4,969,468 A | 11/1990 | Byers et al. |
| 5,010,896 A | 4/1991 | Westbrook |
| 5,016,635 A | 5/1991 | Graupe |
| 5,070,873 A | 12/1991 | Graupe et al. |
| 5,097,828 A | 3/1992 | Deutsch |
| 5,314,423 A | 5/1994 | Seney |
| 5,336,255 A | 8/1994 | Kanare et al. |
| 5,397,338 A | 3/1995 | Grey et al. |
| 5,507,788 A | 4/1996 | Lieber |
| 5,549,656 A | 8/1996 | Reiss |
| 5,674,262 A | 10/1997 | Tumey |
| 5,702,323 A | 12/1997 | Poulton |
| 5,702,429 A | 12/1997 | King |
| 5,843,152 A | 12/1998 | Tu et al. |
| 5,871,526 A | 2/1999 | Gibbs et al. |
| 5,902,328 A | 5/1999 | LaFontaine et al. |
| 6,216,704 B1 | 4/2001 | Ingle et al. |
| 6,266,558 B1 | 7/2001 | Gozani et al. |
| 6,301,500 B1 | 10/2001 | Van Herk et al. |
| 6,324,432 B1 | 11/2001 | Rigaux et al. |
| 6,341,237 B1 | 1/2002 | Hurtado |
| 6,350,276 B1 | 2/2002 | Knowlton |
| 6,480,731 B1 | 11/2002 | DeLuca et al. |
| 6,505,078 B1 | 1/2003 | King et al. |
| 6,567,696 B2 | 5/2003 | Voznesensky et al. |
| 6,829,510 B2 | 12/2004 | Nathan et al. |
| 6,840,955 B2 | 1/2005 | Ein |
| 6,944,503 B2 | 9/2005 | Crowe et al. |
| 7,146,220 B2 | 12/2006 | Dar et al. |
| 7,172,564 B2 | 2/2007 | Bosco |
| 7,204,832 B2 | 4/2007 | Altshuler et al. |
| 7,221,980 B2 | 5/2007 | Kotlik et al. |
| 7,236,832 B2 | 6/2007 | Hemmerling et al. |
| 7,257,448 B2 | 8/2007 | Crowe et al. |
| 7,276,058 B2 | 10/2007 | Altshuler et al. |
| 7,473,251 B2 | 1/2009 | Knowlton et al. |
| 7,483,738 B2 | 1/2009 | Tamarkin et al. |
| 7,499,746 B2 | 3/2009 | Buhlmann et al. |
| 8,216,218 B2 * | 7/2012 | Burns et al. ............ 606/32 |
| 8,265,763 B2 | 9/2012 | Fahey |
| 8,285,381 B2 | 10/2012 | Fahey |
| 8,433,403 B2 | 4/2013 | Fahey |
| 8,588,901 B2 | 11/2013 | Fahey |
| 2002/0049483 A1 | 4/2002 | Knowlton |
| 2002/0143365 A1 | 10/2002 | Herbst |
| 2002/0151951 A1 | 10/2002 | Axelgaard et al. |
| 2003/0229385 A1 | 12/2003 | Elkins |
| 2004/0044384 A1 | 3/2004 | Leber et al. |
| 2004/0173220 A1 | 9/2004 | Harry et al. |
| 2004/0254624 A1 | 12/2004 | Johnson |
| 2005/0288730 A1 | 12/2005 | Deem et al. |
| 2006/0142816 A1 | 6/2006 | Fruitman et al. |
| 2007/0106343 A1 | 5/2007 | Monogue et al. |
| 2007/0178579 A1 | 8/2007 | Brown et al. |
| 2007/0203435 A1 | 8/2007 | Novak |
| 2008/0161883 A1 | 7/2008 | Conor |
| 2008/0195010 A1 | 8/2008 | Lai et al. |
| 2008/0208288 A1 | 8/2008 | Gesotti |
| 2009/0012436 A1 | 1/2009 | Lanferman et al. |
| 2010/0081963 A1 | 4/2010 | Gilhuly |
| 2011/0082517 A1 | 4/2011 | Brezel et al. |
| 2011/0093036 A1 | 4/2011 | Mashiach |
| 2011/0152972 A1 | 6/2011 | Doerr et al. |
| 2012/0226330 A1 | 9/2012 | Kolen et al. |
| 2012/0303076 A1 | 11/2012 | Fahey |
| 2013/0030277 A1 | 1/2013 | Fahey |

FOREIGN PATENT DOCUMENTS

| | | |
|---|---|---|
| JP | 2002-052000 | 2/2002 |
| JP | 2006510431 | 3/2006 |
| KR | 10-866543 B | 11/2008 |
| WO | WO 01/52759 A1 | 7/2001 |
| WO | WO 03/086217 A1 | 10/2003 |
| WO | WO 2004/089185 A2 | 10/2004 |
| WO | WO 2004/098703 A2 | 11/2004 |
| WO | WO 2005/075018 A1 | 8/2005 |
| WO | WO 2005/105203 A1 | 11/2005 |
| WO | WO 2007/017778 A2 | 2/2007 |
| WO | WO 2007/041540 A1 | 4/2007 |
| WO | WO 2007/046886 A1 | 4/2007 |
| WO | WO 2008/032282 A2 | 3/2008 |
| WO | WO 2008/034607 A1 | 3/2008 |
| WO | WO 2008/075250 A1 | 6/2008 |
| WO | WO 2008/116232 A1 | 9/2008 |
| WO | WO 2009/009661 A1 | 1/2009 |

OTHER PUBLICATIONS

Bennie et al.; Toward the optimal waveform for electrical stimulation of human muscle; Eur J Appl Physiol; vol. 88; pp. 13-19; Nov. 2002.

Lacey et al.; Reductions in the amount of time spent in direct patient care by staff nurses in North Carolina; North Carolina Center for Nursing; Aug. 2002.

Lyons et al.; An investigation of the effect of electrode size and electrode location on comfort during stimulation of the gastrocnemius muscle; Medical Engineering & Physics; vol. 26; pp. 873-878; Dec. 2004.

Miklavcic et al.; Electrical Properties of Tissues; Wiley Encyclopedia of Biomedical Engineering; (year of publication is sufficiently earlier than the effective U.S. filing date and any foreign priority date) 2006.

Morris, Peter E.; Moving our critically ill patients: mobility barriers and benefits; Critical Care Clinics; vol. 23; pp. 1-20; Jan. 2007.

Petrofsky et al.; Estimation of the distribution of intramuscular current during electrical stimulation of thequadriceps muscle; Eur J Appl Physiol; vol. 103(3); pp. 265-273; Jun. 2008.

Prausnitz, Mark R.; The effects of electrical current applied to skin: a review for transdermal drug delivery; Advanced Drug Delivery Reviews; vol. 18; pp. 395-425; Feb. 8, 1996.

Rafolt et al.; Dynamic force responses in electrically stimulated triceps surae muscles: effects of fatigue and temperature; Artificial Organs; vol. 23; No. 5; pp. 436-439; May 1999.

Solomon et al.; The effects of TENS, heat, and cold on the pain thresholds induced by mechanical pressure in healthy volunteers; Neuromodulation; vol. 6; No. 2; pp. 102-107; Apr. 2003.

Stecker et al.; Mechanisms of electrode induced injury. Part 1: theory; Am. J. End Tech.; vol. 46; pp. 315-342; Dec. 2006.

Snyder-Mackler et al.; Use of electrical stimulation to enhance recovery of quadriceps femoris muscle force production in patients following anterior cruciate ligament reconstruction; Phys Ther.; 74(10):901-7; Oct. 1994.

Suganuma et al.; Measurement of Tension of tendon tissue based on electrical impedance; J. Ortho Science; vol. 9; pp. 302-309; (year of publication is sufficiently earlier than the effective U.S. filing date and any foreign priority date) 2004.

Zanotti et al.; Peripheral muscle strength training in bed-bound patients with COPD receiving mechanical ventilation: effect of electrical stimulation; Chest; vol. 124; No. 1; pp. 292-296; Jul. 2003.

Fahey et al; U.S. Appl. No. 13/926,827 entitled "Devices and Systems for Stimulation of Tissues" filed Jun. 25, 2013.

Covidien; Principles of Electrosurgery (white paper); p. 3; accessed from http://www.asit.org/assets/documents/Prinicpals_in_electrosurgery.pdf on Dec. 12, 2012, 4 pages.

XODUS Medical; Electrosurgery Frequency Spectrum; accessed from http://www.xodusmedical.com/Modules/Product/Product-Training.aspx?Launch=Electrosurgical on Dec. 12, 2012; 1 page.

\* cited by examiner

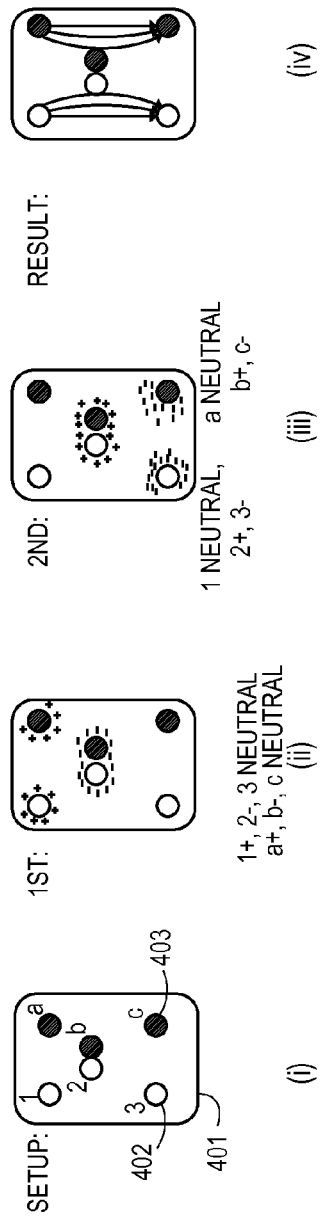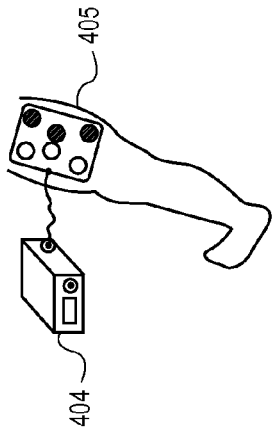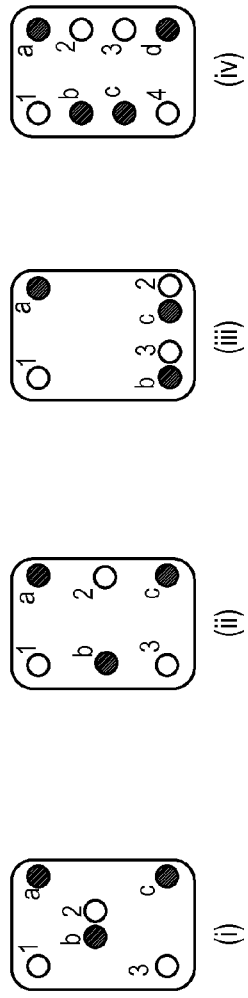
FIG. 4A
FIG. 4B
FIG. 4C

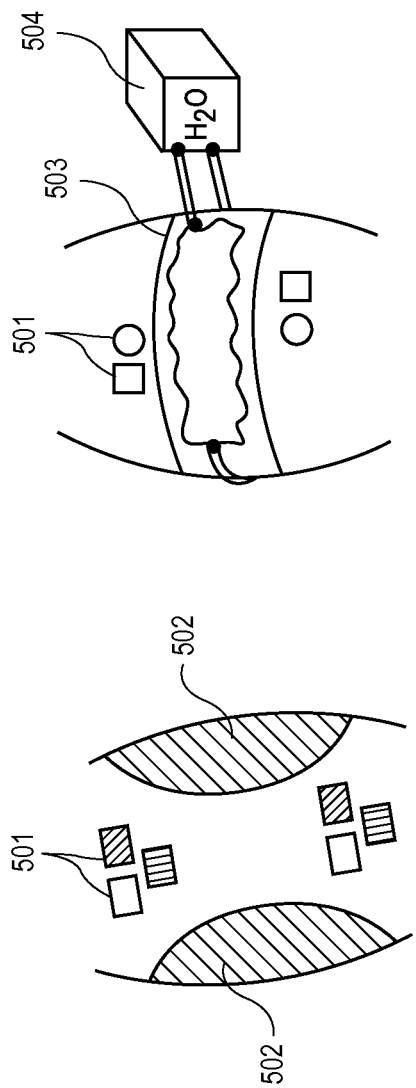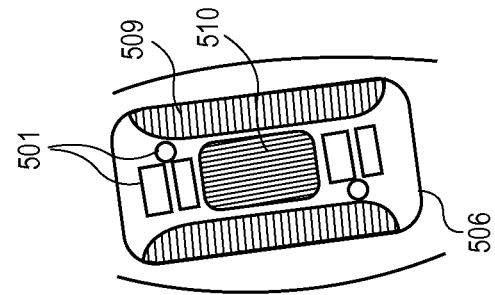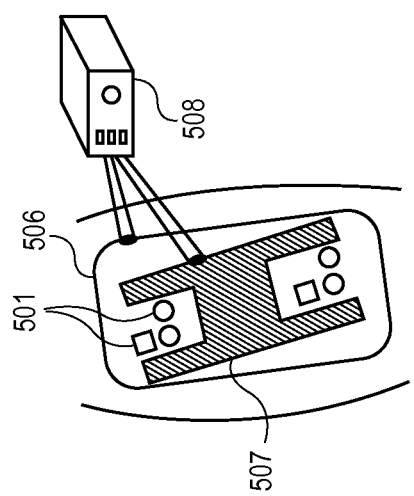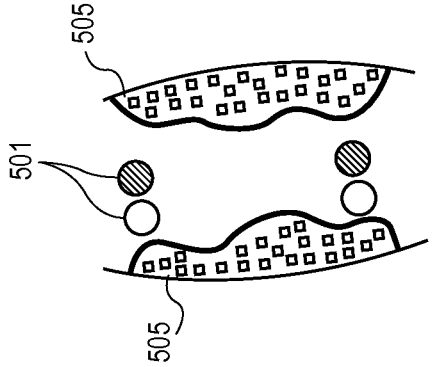

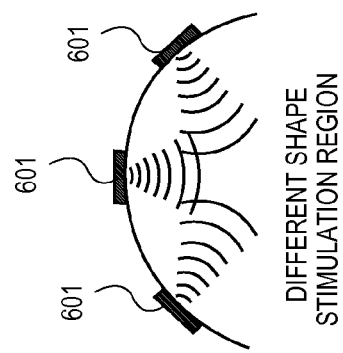
FIG. 6A STANDARD PLACEMENT
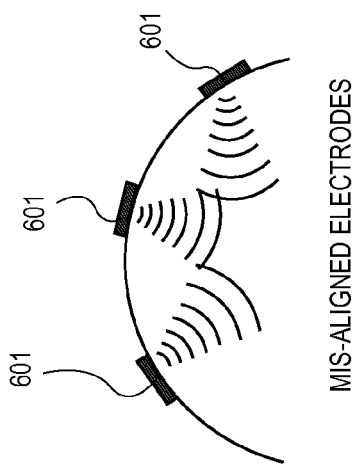
FIG. 6B MIS-ALIGNED ELECTRODES
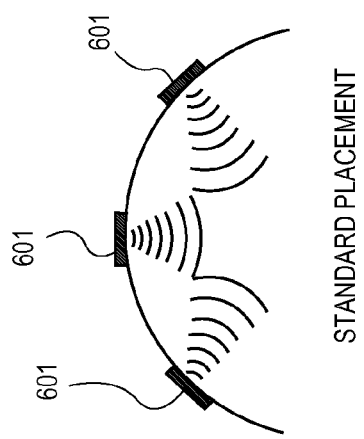
FIG. 6C DIFFERENT SHAPE STIMULATION REGION
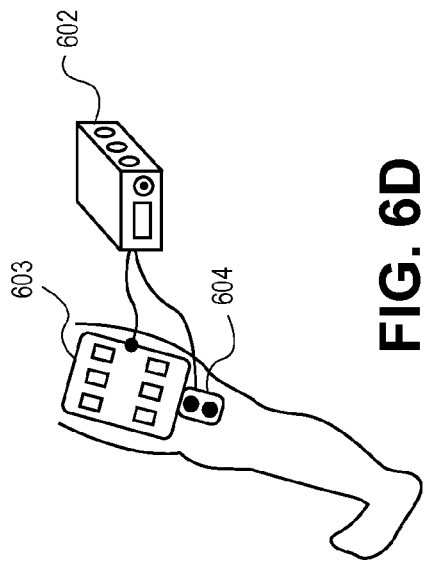
FIG. 6D

SYNERGISTIC MUSCLE ACTIVATION DEVICE

CROSS-REFERENCE TO RELATED APPLICATIONS

This application is a divisional of U.S. patent application Ser. No. 12/943,486, filed Nov. 10, 2010, now U.S. Pat. No. 8,588,901, which application claims the benefit of U.S. Provisional Patent Appln. No. 61/260,324, filed Nov. 11, 2009, both of which are incorporated herein by reference.

This application is related to U.S. patent application Ser. No. 12/710,243, filed Feb. 22, 2010, which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Neuromuscular electrical stimulation ("NMES") (also referred to as powered muscle stimulation, functional muscle stimulation, electrical muscle stimulation, and other terms) has several therapeutic uses, including pain relief, prevention or retardation of disuse atrophy, and improvement of local blood circulation. NMES is typically delivered as an intermittent and repeating series of short electrical pulses. In many implementations, these pulses are delivered transcutaneously by surface electrodes that are attached to a person's skin. Electrodes may be held to the skin through the use of straps, adhesives, or other mechanisms, and often contain a coupling layer composed of hydrogel that is capable of enhancing the efficiency of energy transfer from the electrode to the skin and underlying tissues.

A known drawback to the use of NMES with surface electrodes is user discomfort. As energy is transmitted to muscle tissues by surface electrodes, it passes through the skin and through superficially-located sensory nerves. As the activation threshold for these sensory nerves is generally lower than that of the motor nerves that control muscle activation, these nerves are usually innervated during NMES. This sensory excitation may cause discomfort in the form of a 'pins and needles' or similar sensation. For many users this sensation is uncomfortable, and in some, it is intolerable even when they consider the long-term benefits of NMES. Thus, discomfort impacts user compliance and can limit NMES effectiveness, for example by limiting energy levels used to those that the patient can tolerate instead of those that are most therapeutically useful. It has been the goal of several investigations to improve comfort during NMES through adjustments to electrode size, electrode placement location, stimulation waveform parameters, and other mechanisms (for example, see Bennie et al., Eur J Appl Physiol 88 (2002), Baker et al., Clin Ortho Research 233 (1988), and Lyons et al., Med Eng Phys 26 (2004), all incorporated herein by reference).

The amount of discomfort induced by NMES through sensory nerve activation is related to the current density in superficial tissue regions. Without wishing to be bound by any theory, it is thus believed that comfort can be improved by reducing current density in superficial regions of tissue. However, using muscle stimulation devices and methods described in previous investigations, this reduction of superficial current density would lead to a corresponding loss of current density in deeper tissue regions that contain muscle tissues. This loss in deep-tissue current density will produce weaker muscle contraction, which in many cases will diminish the benefits of NMES therapy.

In U.S. Pat. No. 4,580,569 to Petrofsky teaches a multi-electrode and multi-channel approach to reducing current density in superficial tissues while achieving greater current density in moderately deeper tissues. Specifically, Petrofsky teaches a method to use skin surface electrodes to stimulate a first muscle region that lies anatomically deeper than a second, more superficial muscle region, without stimulating contraction in said superficial muscle region. Two electrode sets are used that each provide a given amount of current, with the provided current from each electrode set being lower than the threshold level needed to activate superficial muscles. However, the two electrode sets are arranged (and potentially timed) in such a way that the two sources of energy combine at depth, and through superposition create enough current density to cause contraction of the deeper muscle region. The general method is illustrated graphically in FIG. 1.

The teachings of U.S. Pat. No. 4,580,569 are not, however, sufficient to achieve optimal discomfort reduction during NMES. For example, while the devices and methods disclosed by Petrofsky have some utility for small electrode separation distances and relatively shallow target muscle groups (the examples of hand and wrist muscles are provided in the specification), they will perform extremely sub-optimally for discomfort reduction during stimulation of larger and deeper muscle groups if it is desired not to compromise the degree of muscle activation in deeper muscles. This sub-optimal performance is related in part to lateral energy spreading, a phenomena that increases in severity as electrode separation distances are large. For larger and/or anatomically-deep muscle groups (e.g., quadriceps), electrode separation distances are most suitably 10-15 cm to achieve deep-penetration of energy (see Petrofsky et al., Eur J Appl Physiol 103 (2008), incorporated herein by reference). This separation distance will cause for a three-dimensional spread of energy from both electrode pairs, with a portion of the applied energy from each electrode pair traveling through tissue regions in a way that it cannot combine with energy from the other electrode pair. This concept is illustrated generally in FIG. 2(a). Thus, there is inherent inefficiency in the process. Due to this inefficiency, large current densities must be utilized at each electrode pair.

What are needed are more efficient muscle stimulation systems and their methods of use.

SUMMARY OF THE DISCLOSURE

The disclosure generally describes muscle stimulator systems and methods of use that provide comfort improvements by using energy delivered to a person more efficiently. For example, by reducing or eliminating effects related to lateral energy spreading from independent electrode pairs, more of the original energy applied by each electrode pair can combine to elicit contraction of a deep muscle tissue. Thus, a lower amount of delivered energy may be used to achieve a target amount of muscle activation. Without wishing to be bound by any theory, it is believed that lowering the amplitude of delivered energy will lead directly to improvements in user comfort and safety.

An exemplary disadvantage of existing NMES devices and technologies is that they do not include mechanisms that are useful for reducing the lateral spreading of energy that occurs between pairs of electrodes. As a result, existing technologies do not provide mechanisms for energy concentration in muscle tissues using multiple electrode pairs. Accordingly, discomfort reduction using these devices and methods is suboptimal. In addition, the existing technologies do not adequately teach other mechanisms for comfort improvement during NMES without performance losses. An exemplary advantage of devices, systems, and methods of use described herein is that patient comfort during NMES is improved without sacrificing performance. In some embodiments of the presently-disclosed devices, systems, and methods of this, this exemplary advantage is achieved in part by reducing the energy density required to achieve a given degree of muscle contraction. Specifically, the required energy density in superficial tissues is reduced. An additional exemplary advantage of the present disclosure is improving the safety of NMES by reducing energy requirements, as increasing the amplitude of delivered energy (and thus the current density in tissue) increases the risk of burns, nerve and/or muscle damage, and other potential complications (as detailed by Prausnitz *Advanced Drug Delivery Reviews* 18:395-425, 2006 and Stecker et al *Am J END Tech.*, 43:315-342, 2006, both of which are incorporated herein by reference). An additional exemplary advantage of the present disclosure is improving the performance of NMES, specifically in challenging stimulation subjects (including but not limited to overweight obese, elderly, or edematous persons) where oftentimes the maximum amplitude of energy considered safe for use is necessitated to achieve even minimal muscle contraction. In this group of individuals, more efficient use of delivered energy will improve the degree of muscle contraction achievable and thus increase the beneficial effects of NMES therapy.

Some embodiments of the methods disclosed herein include several steps that will allow for more efficient transfer of electrical energy to deep-lying muscle tissues while minimizing energy density in superficial tissues. In some implementations of the methods, a first step involves placing two or more pairs or groups of electrodes on the surface of the skin in the vicinity of the muscle it is desired to stimulate. A subsequent step comprises combining the electrodes with specialized electronics or another mechanism to help prevent the lateral spreading of energy. A third step comprises delivering electrical stimulation therapy to the subject by applying stimulation energy to the surface electrodes.

In some embodiments of a stimulation system and method, a rapid switching technique is implemented to change the relative polarity of electrode pairs or groups. Switching electrode polarity in a way such that electric fields shift faster than electrical current travels in body tissues may allow for guidance of stimulation energy along predetermined, efficient pathways. Guidance of energy in this manner may allow for a decrease in the level of current density required in superficial regions to achieve significant muscle contraction in deeper regions, thus improving comfort and safety.

In some embodiments, temperature gradients are utilized to change the electrical impedance of tissues in predetermined anatomical regions. For example, superficial cooling may be applied to a person in a manner such that a temperature gradient (for example, of 5° C. or greater) exists between the skin and anatomically deeper tissues. For temperatures below 40° C., tissue impedance decreases by about 2%/° C. (see Miklavcic et al., *Electrical Properties of Tissues*, Wiley Encyclopedia of Biomedical Engineering, 2006, incorporated herein by reference), and thus the existence of this temperature gradient will in turn provide shifts in the intrinsic electrical resistance of tissues that mimic the temperature gradient's shape. As applied electrical energy will be distributed proportionally along paths of lower tissue resistance, energy will preferentially be deposited in non-cooled regions of tissue. Accordingly, the synergistic combination of energy from multiple electrode pairs may be more precisely controlled than when electrode pairs are not used in conjunction with a mechanism to prevent lateral spreading of energy. This increased precision with regard to the directionality of energy delivered from multiple electrode pairs will allow for adequate muscle stimulation using lower superficial energy densities. In alternative embodiments, heating tissues in specific anatomical locations will produce a similar impedance gradient and thus also result in decreased lateral spreading of electrical stimulation energy. In alternative embodiments, both tissue heating and cooling are used to alter the intrinsic electrical impedance distribution of tissue.

In alternative embodiments, mechanisms other than temperature change are used to alter the intrinsic electrical impedance of predetermined regions of tissue. For example, topical or injected chemical substances may be utilized to create impedance gradients similar to those created with strategically-induced thermal gradients in tissue. For example, an aerosol or similar spray can be applied to skin that temporarily changes its conductive properties. Alternatively, an electric/magnetic/electro-magnetic field generation device that electrically polarizes cells is used to alter their natural conductance. Alternatively a pressure-generating device can be used to compress cells and/or move excess edematous fluid away from the region of interest.

In some embodiments, an alternating or static magnetic field is used to influence the direction of applied electrical energy to the body and thus decrease the amount of lateral energy spreading between electrodes. Without wishing to be bound by any theory, it is believed that when placed in suitable predetermined locations and timed precisely to the delivery of energy to pairs or groups of surface electrodes, the magnetic field (or changes in said magnetic field) can be used to produce noticeable changes in the energy distribution between surface electrodes. Impacting energy distributions between two or more pairs or groups of surface electrodes simultaneously may allow for improvements in the combined delivery of energy in non-superficial muscle tissues.

In some embodiments improved combination of stimulation energy from two or more pairs or groups of electrodes is achieved with advanced timing control that is based upon sensor feedback. While U.S. Pat. No. 4,580,569 teaches that energy delivery phase delays may improve synergistic combination at depth, a predetermined static (i.e., fixed) delay is specified. This method is not optimal for larger muscle groups where electrode placement and local anatomy may vary considerably from operator to operator (and/or user to user). Accordingly, some embodiments cycle through a default series of stimulation events using different phase delay intervals between energy pulses delivered by different pairs or groups of electrodes. Sensor feedback (for example, EMG, accelerometer, or more advanced custom sensors) are utilized to determine which delay profile is most suitable to provide muscle stimulation to a given body region of a user. Since the delay profile is now optimized for the successful superposition of energy levels at depth, the total energy density in superficial tissues may be reduced and comfort improved.

In some embodiments of the devices, systems, and methods disclosed herein, comfort during NMES may be improved by interfering with or influencing the normal mechanisms of pain generation in the region of stimulation. For example, certain types of applied electrical energy are known to serve better for pain relief than for inducing muscle contraction. As an example, consider waveforms utilized during transcutaneous electrical nerve stimulation (TENS), which tend to be higher in repetition frequency and lower in amplitude than energy waveforms applied during NMES. By combining TENS and NMES energy in a specific manner, it may be possible to eliminate or greatly reduce 'pins and needles' discomfort associated with delivery of NMES energy. In some embodiments, both types of energy are delivered via the same surface electrodes by multiplexing output from a pulse generation device. Also, in some embodiments, electrical waveforms associated with both pain relief and muscle stimulation effects do not interact in a superposition-like manner (i.e. electrical current applied to the body is dissimilar to interferential current mechanisms that are commonly described in the prior art).

In some embodiments, a topical analgesic (such as those containing NSAIDs or capsaicin) and/or local anesthetic (e.g., lidocaine) is used in combination with stimulation electrodes to dull or eliminate uncomfortable sensations related to applied energy activating superficial sensory nerves. In some embodiments, the analgesic or anesthetic delivery mechanism is built directly into a surface electrode (for example, is mixed in with a hydrogel layer that contact the skin) so as not to create an additional step required for an operator to undertake.

A some embodiments of the system includes three components: surface electrodes that are used to couple electrical energy into and out of the body, a mechanism to improve comfort of NMES, and a stimulation control unit that creates the stimulation energy pulses and delivers them to the surface electrodes. The control unit communicates with the surface electrodes is a manner suitable for transmitting and receiving electrical signals, such as with a standard cable connection, a wireless connection such as Blue-tooth, WiFi, infrared, or other similar connections.

Some embodiments comprise custom stimulation pads that include surface electrodes placed in predetermined configurations. Custom stimulation pads will be configured to include and/or interface with both electrodes and also comfort improvement mechanisms. For example, in some embodiments the stimulation pad may include electronics to allow for rapid polarity switching of electrodes. As a second example, variations implement a stimulation pad that may include mechanisms to apply superficial temperature gradients in predetermined places of the body in the proximity of the region to where NMES is applied. In variations, discrete stimulation electrodes are utilized by the system. In some embodiments, the user has full control over the relative placement of surface electrodes and/or comfort improvement mechanisms.

In some embodiments, the control unit includes custom electronics, memory, and control features to deliver electrical stimulation energy to surface electrodes. The control unit includes a power source (ex. battery or isolation transformer for use with mains power), a voltage/current amplifier, a microcontroller, FPGA, and/or other control mechanism, timing circuitry, and waveform generation circuitry. In some embodiments, the control unit includes memory and/or additional signal processing circuitry for more advanced control over electrical stimulation waveforms. In variations, sensors coupled to the person receiving NMES are utilized to record data indicative of muscle contraction, and data sampling and feedback control systems within the control unit are used for closed-loop optimization of parameters describing stimulation energy waveforms, such as the phase delay between signals applied to different pairs or groups of surface electrodes.

An exemplary advantage of the devices, systems, and methods of use is that they will enable effective NMES therapy in a subset of persons where NMES is ineffective due to poor user compliance or from the user being unable to tolerate the high energy levels required for quality muscle contraction when using technology specified in the prior art. For example, many muscle stimulators currently on the market include 'user compliance meter' features, where a physician, physical therapist, or equivalent can determine if a user has been engaging in NMES as prescribed. The existence of such features illustrates the widespread nature of the discomfort problem. By providing mechanisms to improve comfort during NMES, this proven therapy will be successfully applied to a greater number of persons.

An additional exemplary advantage of the devices, systems, and methods disclosed herein is that they will improve safety during NMES. Specifically, embodiments that allow for more efficient use of energy (and thus require lower energy use overall) will decrease risk associated with burns, muscle and/or nerve damage, and other types of injury.

BRIEF DESCRIPTION OF THE DRAWINGS

FIGS. 4(a)(i)-4(c)(iv) provide an overview of the rapid-switching embodiment functionality, as well as several example implementations thereof.

FIGS. 5(a)-(e) provide exemplary embodiments that utilize temperature gradients.

FIGS. 6(a)-(d) provide an overview of situations where fixed phase delays between stimulation channels are non-ideal, and an explanation of why precise timing control is important. Also shown is an example embodiment of a device, system, and method of use.

DETAILED DESCRIPTION OF THE DISCLOSURE

Figure 1:
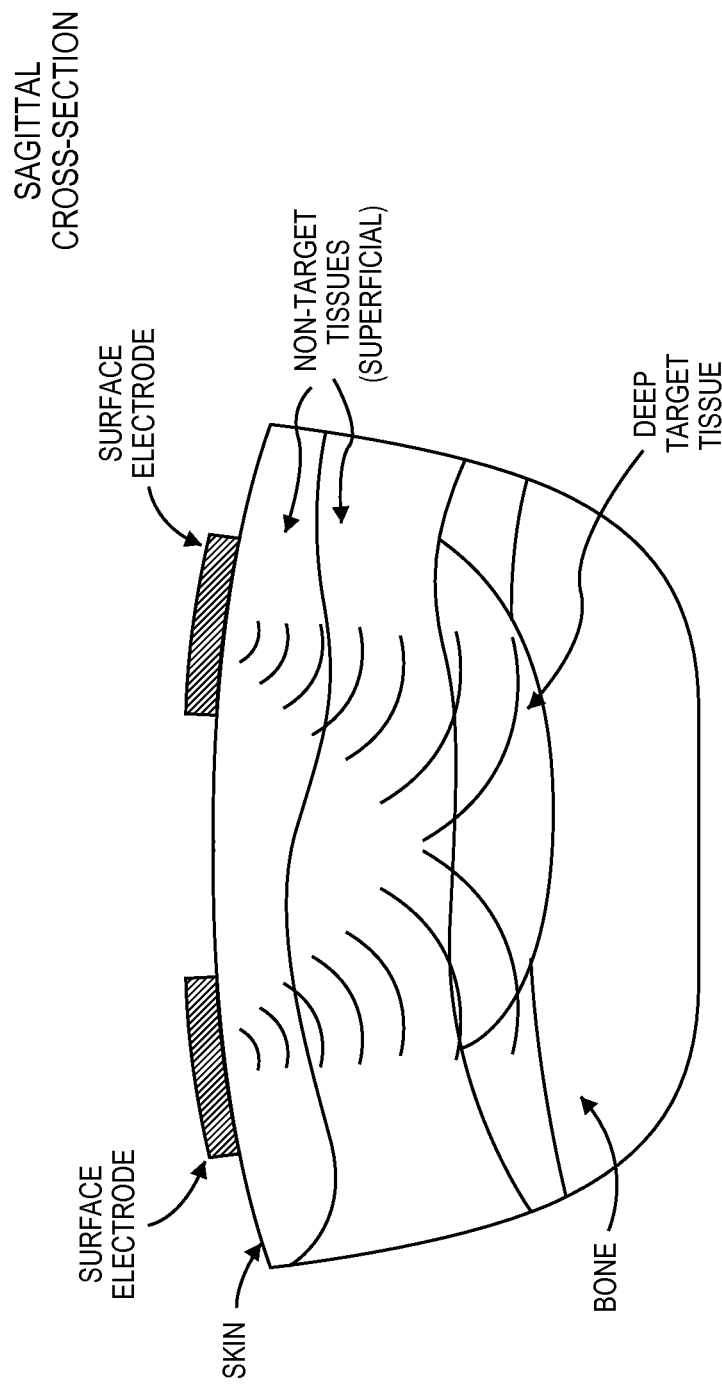
FIG. 1 illustrates existing techniques, wherein energy from two pairs or groups of surface electrodes can be combined at depth.

The disclosure herein provides systems and methods for neuromuscular electrical stimulation of muscle and/or nervous tissue using mechanisms to improve user comfort. Various aspects of the disclosure described herein may be applied to any of the particular applications set forth below or for any other types of electrical stimulation and sensing systems or methods. The invention may be applied as a standalone system or method, or as part of an integrated medical treatment system. It shall be understood that different aspects of the disclosure can be appreciated individually, collectively, or in combination with each other.

In some embodiments, the system includes at least components: surface electrodes that are used to couple electrical energy into and out of the body, a mechanism, device, or method to improve comfort during energy application, and a stimulation control unit that creates the stimulation energy pulses and delivers them to the surface electrodes. In some embodiments, the stimulation electrodes are assembled into a custom stimulation pad such that electrode layout and configuration will be pre-optimized for a particular region of the body. The control unit communicates with the stimulation pad through a wired connection, radiofrequency transmission, optical, acoustic, or electromagnetic signals, or another suitable mechanism. The control unit is a separate unit that may be located some distance from the person receiving therapy. In an alternate embodiment, the control unit may be integrated into a housing unit comprising the stimulating electrodes and/or surface cooling components.

In some embodiments, the control unit includes components such as a signal generator, memory, processor, and power supply. The primary operation of the control unit may be provided by a microprocessor, field programmable gate array (FPGA), application specific integrated circuit, some combination of these mechanisms, or another suitable mechanism. When activated, the control unit generates electrical stimulation signals that are transmitted to the surface electrodes in the stimulation pad, which couple the energy into the body to activate muscles. Some electrical stimulation parameters, including the duration of therapy, may be adjustable by the operator through buttons, knobs, dials, or switches on the control unit. Other electrical stimulation parameters, such as stimulation pulse energy amplitude and phase delay between pulses applied to different pairs or groups of electrodes, may be adjusted by the user through control unit controls or may be automatically optimized using automatic algorithms implemented by the control unit. In some embodiments, the control unit also fundamentally controls at least some aspect of the mechanism implemented to improve user comfort.

In some embodiments, the control unit is capable of transmitting stimulation pulses on at least 2 and preferably many more (ex. 8-10) channels simultaneously and independently. In many cases, applying current to two or more pairs or groups of electrodes independently is advantageous to simply splitting the current from a single channel across two or more parallel electrode configurations. In the situation where current from a single channel is split (i.e. two or more electrode pairs receiving the signal are not receiving independent energy signals) between two or more electrode pairs, equal distribution of the original energy is not guaranteed. For example, without wishing to be bound by any theory, it is believed that if about 40 mA of supply current is split between two electrode pairs, perfect balancing of electric impedance between each electrode pair is required if about 20 mA will travel along each route. This situation of balanced impedance pathways is unlikely to occur in vivo. In addition to the ability to transmit stimulation pulses on independent channels simultaneously, some embodiments of the control unit are also capable of creating arbitrary phase delays between pulses originating from different channels.

In some embodiments, the stimulation pad is comprised of a thin and flexible housing with an adhesive hydrogel backing to facilitate maintenance of skin contact with the person receiving NMES. The hydrogel backing will also enhance the coupling of electrical energy and signals between stimulation electrodes and the person's body. Hydrogel backing may allow for skin adhesion in the regions including electrodes or in larger regions. The stimulation pad will be configured to include or interface with mechanisms, devices, and/or methods to improve comfort during energy delivery. The stimulation pad includes two or more strategically-placed surface electrodes that are used to deliver electrical energy to muscles and/or nerves in order to produce muscle contraction.

In some embodiments, the stimulation electrodes are arranged in an array with a predetermined layout (see, for example, FIG. 3). In some embodiments, the stimulation electrodes are arranged in a configurable array. The array may be configurable such that, at any given time, only a subset of the electrodes in the array may be actively delivering energy to a person receiving NMES. However, electrodes inactive for energy delivery may still be configured to deliver relevant information (such as the electrical impedance between it and a second electrode in the array) to the control unit. In a variation embodiment, the stimulation pad may include only 2 stimulation electrodes, with both electrodes being active during NMES energy delivery. In another variation embodiment, the surface electrodes may not be contained in a larger stimulation pad. Instead, discrete electrodes of any size or shape could be utilized by an NMES operator and placed in the position deemed by the operator to be most suitable.

In some embodiments, two or more groups of electrodes are arranged in specific patterns on a stimulation pad (see, for example, FIG. 4). The stimulation pad, control unit, or both include electronic components that allow for rapid switching of the polarity of specific electrodes in the group. To be successful, the electric field created by voltage differences between electrodes must be altered on a time-scale that is faster or similarly fast as current travels through tissue between electrodes. Given that modern electronics allow for nanosecond switching of electrical components and signals, it is believed that this is readily achievable. Initially, electronics in the control unit apply a voltage potential between two electrodes in a given group of three or more electrodes. This voltage potential creates a flow of current that travels broadly between the two electrodes. After a very short time following injection of current into tissue (due to the voltage potential between electrodes), the relative polarity of electrodes in the group is shifted by electronic switching components (controlled by software, firmware, or hardware based timing means), causing the direction of current flow to be altered.

By way of a simplified example, referring to FIGS. 4(a)-(c), initially electrode 1 may be relatively positively charged, while electrode 2 may be relatively negatively charged, while electrode 3 may be neutral. This creates a current flow between electrodes 1 and 2. After a very short period of time (determined by the separation distance between electrodes), electrode 1 becomes neutral, while electrode 2 is given a relatively positive charge and electrode 3 is given a relatively negative charge. This step creates current flow between electrodes 2 and 3. In total, when timing is precisely correct, in essence current travels between electrodes 1 and 3 with a bend in direction towards electrode 2. Minor alterations to the method (for example, adding slight charge to the neutral electrode) allows for further tuning of total current injection and direction. Specific configurations of electrode groups used ensure penetration of applied current to deep muscle tissues. Through increased control of current directionality, lateral spreading of applied energy can be minimized or contained in a constructive way, increasing the efficiency of the NMES device and thus reducing the amount of current density needed in superficial regions to induce muscle contraction in deeper regions. This method will improve comfort during NMES energy delivery.

In some embodiments, two or more pairs or groups of electrodes are utilized during NMES in conjunction with a mechanism allowing for the transfer of thermal energy. The mechanism may be an active source of thermal energy (for example, a heating or cooling device), or a passive conduit for energy (for example, a heat sink mechanism). The embodiment may achieve improved user comfort by warming, cooling, or selectively warming and cooling tissue region(s) in proximity to the location of NMES delivery. In one implementation of this embodiment, cold temperatures are applied to body regions in the lateral edges of the electrode configuration (see, for example, FIG. 5). In some implementations, cold may also be applied to the region of body tissue in between electrode regions. Application of cold temperatures will increase tissue electrical impedance, proportionally reducing energy distribution in these regions. Effectively, cold application forces a greater proportion of energy delivered by surface electrodes to more central regions, where tissues are warmer, thereby reducing the lateral spreading of current. More of the initial energy from each pair or group of electrodes used to transmit energy into the body enters into the overlapping region between electrode pairs or groups, and thus the total sum of energy reaching target muscle tissues is improved. This improvement allows for lower energy levels to be used initially, reducing current density in superficial tissues and increasing comfort during NMES.

In a variation embodiment, a stimulation pad is configured to house or interface with electronics capable of generating a static or dynamic magnetic field. It is known that the direction of a charged particle traveling through a magnetic field will be influenced by the presence of the field. Without wishing to be bound by any theory, it is believed that the presence of a precisely located, sufficiently strong, and properly timed magnetic field may further assist in preventing or reducing the lateral spread of current traveling between surface electrodes. As noted above, any reduction in lateral spreading of energy will improve the efficiency of coordination between energy applied by different pairs or groups of electrodes, thus lowering the total amount of energy required to achieve a desired degree of muscle contraction.

In some embodiments, two or more pairs or groups of electrodes are utilized in conjunction with a sensor system (see, for example, FIGS. 6(a)-(d)). The sensor system (for example EMG, strain gauge, accelerometer, temperature sensor, sensor measuring another parameter descriptive of muscle contraction, etc.) attaches to the body of the user in the vicinity of the target muscle group and is positioned in a manner so as to be capable of producing an output that is indicative of the degree of muscle contraction induced through the application of energy during NMES. The sensor system remains in communication with the control unit through a wired connection or other suitable means. During operation, stimulation signals are delivered near-simultaneously to two or more pairs or groups of electrodes, with energy from each electrode set cooperating in an additive way at depth to activate a target muscle. The term near-simultaneously is used to indicate a slight (ex. 0.3-10 ms) phase delay between signals originating from different electrode pairs or groups. During energy application, the sensor(s) measure parameters that are indicative of the degree of contraction produced in the target muscle tissue. Feedback from the sensor(s) is used to adjust and optimize the phase delay between signals applied by different electrode sets in order to improve energy cooperation at depth. In an example embodiment, the control unit initiates NMES by cycling through a default series of stimulation/sensing events using a predetermined series of phase delay shifts between channels. The phase delay profile that produces the strongest muscle contraction is chosen for use during NMES. In a variation of this embodiment, a processor in the control unit calculates an ideal delay profile given sensor data (for example by interpolating data between the two phase delay profiles that performed the best), thus allowing for a final phase delay profile that was not initially programmed into the control unit. As mentioned previously, the ideal phase delay will optimize energy coordination at depth, lowering the total energy that is required to produce a given degree of muscle contraction. These lower current density requirements will improve both the comfort and safety of NMES.

In some embodiments, multiple energy waveforms are used in conjunction with one another to reduce discomfort during stimulation. In one example embodiment, one or more independent channels are in electrical communication with each electrode pair or group utilized. Accordingly, at least two types of electrical energy are applied by the control unit: a first stimulation waveform capable of achieving local pain relief (for example, waveforms commonly associated with TENS) and at least one additional waveform, such as those typically used to induce muscle contraction during NMES. Generally speaking, waveforms during TENS tend to have higher pulse repetition frequencies and lower amplitude than those used during NMES. This combination approach to energy delivery will allow for simultaneous pain relief and induced muscle contraction, thus improving comfort during NMES therapy.

In some embodiments, each electrode set or pair is capable of applying both types of electrical waveforms to the body. This is a significant advance over devices and methods disclosed in the prior art because in many desired stimulation locations (ex. triceps or quadriceps), there exists limited space to place electrodes. Thus, if separate electrodes are necessitated to deliver pain-relief waveforms, less space is available for electrodes that deliver muscle-activating waveforms. Low current density energy from different sets of electrodes can combine synergistically at depth to produce a high current density in target regions, and thus using a greater number of electrode sets to deliver muscle-activating waveforms decreases the energy density required to be delivered by each (and thus increases comfort). Therefore it is desirable to not occupy any available electrode space in the intended region of stimulation by separate electrodes that apply only pain-relief waveforms. It is notable that reducing electrode size so that more electrodes may fit in one region is not a practical option, since comfort in general is proportional to electrode size. In the preferable embodiment presently described, both pain-relief and muscle-activating waveforms are multiplexed for application by the same set of electrodes (see, for example FIGS. 7(a)-(c)). This multiplexing process may be repeated by several sets (i.e. pairs or groups) of electrodes in a given stimulation region.

In a variation of the embodiments described in the previous paragraph, specially-placed electrodes deliver pain-relief electrical waveforms while additional, separate electrodes provide muscle stimulation waveforms. In certain scenarios, extremely localized pain relief waveform stimulation may provide superior comfort improvement relative to more widespread distribution of applied energy. Without wishing to be bound by any theory, it is believed that this may be the case for challenging stimulation subjects (e.g., obese/overweight, edematous, elderly) that require large amounts of total energy applied to skin electrodes.

In some embodiments, a topical analgesic and/or anesthetic is utilized in conjunction with surface electrodes to decrease discomfort related to excitation of superficial sensory nerves. In one implementation, a lidocaine (or similar, ex. capsaicin or other NSAID) paste or gel is manufactured into or layered below (skin contact side) of the hydrogel contact layer of the surface electrodes utilized during NMES. Thus, when electrodes make contact with the skin, the analgesic/anesthetic is automatically applied without extra steps for the operator. In variation embodiments, the topical analgesic/anesthetic is applied in discrete locations by an operator prior to placement of stimulation electrodes or a stimulation pad. In some embodiments using analgesics/anesthetics, additional safety features (such as thermistors, thermocouples, or other mechanisms aimed at burn prevention) are implemented to account for use of NMES over areas of insensate skin.

The methods described herein can be utilized effectively with any of the embodiments or variations of the devices and systems described above, as well as with other embodiments and variations not described explicitly in this document.

DESCRIPTION OF THE FIGURES

FIG. 1 illustrates an existing technique to stimulate contraction in a deep muscle tissue without eliciting contraction in more superficial muscle tissues. As shown in the cross-sectional view, the energy from two separate pairs or groups of surface electrodes is combined in a coordinated fashion at depth. Each pair or group applies an energy level that is presumably too weak to cause contraction on its own. However, when the two energy deposits overlap in the target region, they combine in a way to produce an energy level that surpasses the threshold for muscle contraction in that region. Also, because current density is reduced in the region of superficial sensory nerves, comfort can also be improved using this method.

Figure 2A:
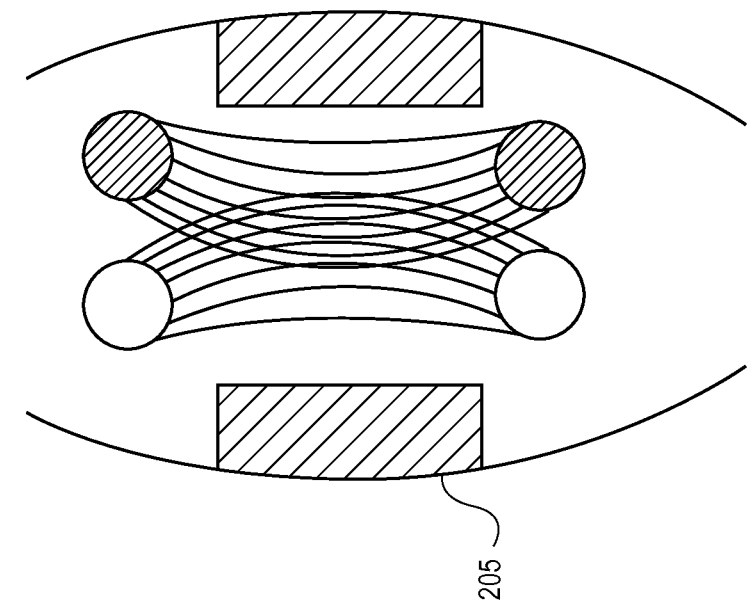
FIG. 2(a) illustrates existing techniques wherein lateral energy spreading limits the efficiency of energy transfer.

FIG. 2(a) illustrates an existing technique and illustrates why the technique is not sufficient to optimally reduce the energy requirements of stimulation. FIG. 2(a) shows a bird's eye view of region of stimulation using two electrode pairs (labeled 201 and 202, respectively). As energy travels between the two electrodes in a pair, energy spreads in three dimensions. In this two-dimensional sketch, the lateral spread of energy is represented by field lines (203). As shown, energy traveling between electrodes with moderate separation distances can spread significantly laterally, with an appreciable percentage of the original energy traveling along a pathway where it cannot combine synergistically with energy from the other electrode pair. In FIG. 2(a), the region inside the bold outline (204) indicates where energy from the two pairs of electrodes overlap.

Figure 2B:
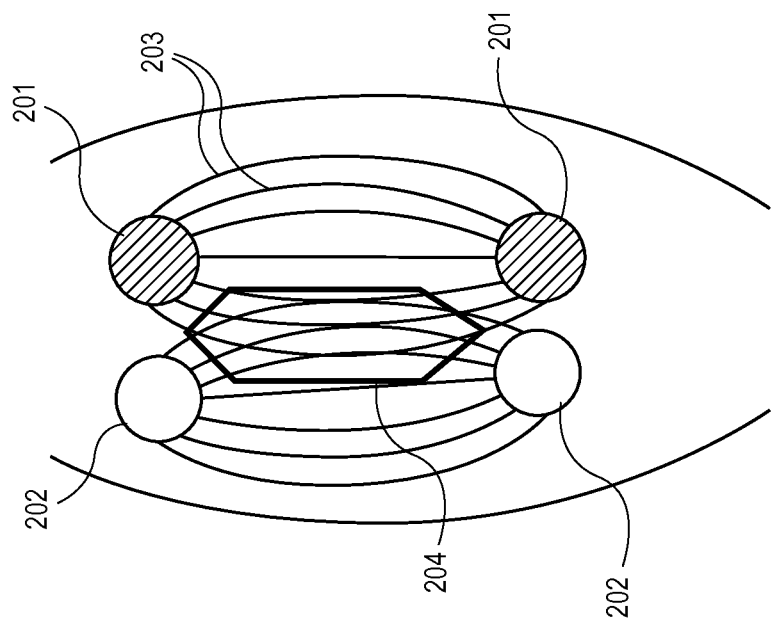
FIG. 2(b) illustrates an exemplary embodiment in which exemplary impedance modification elements reduce the outward direction lateral spreading of energy.
Figure 3D:
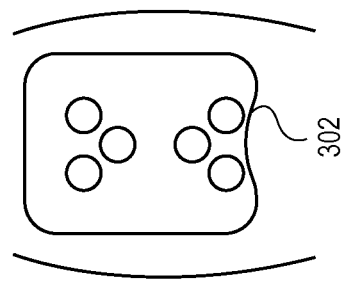
FIGS. 3(a)-3(g) illustrate several example layouts of electrode arrays implemented on a stimulation pad.
Figure 3G:
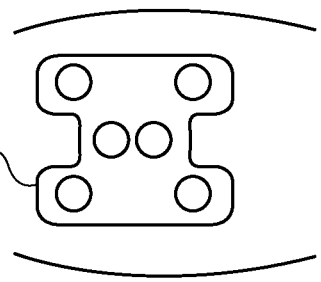
Figure 3C:
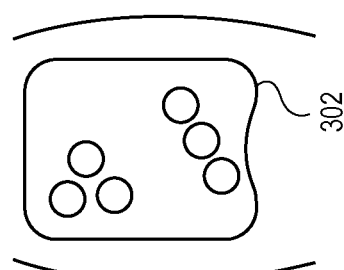
Figure 3F:
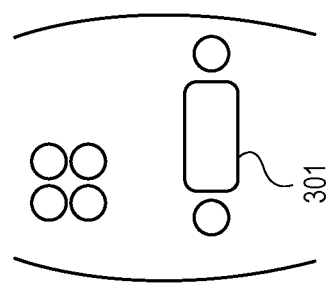
Figure 3B:
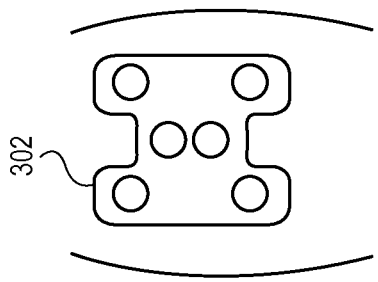
Figure 3E:
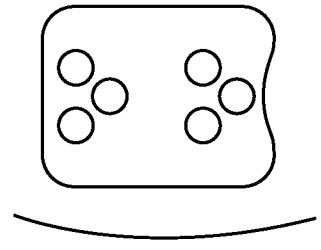
Figure 3A:
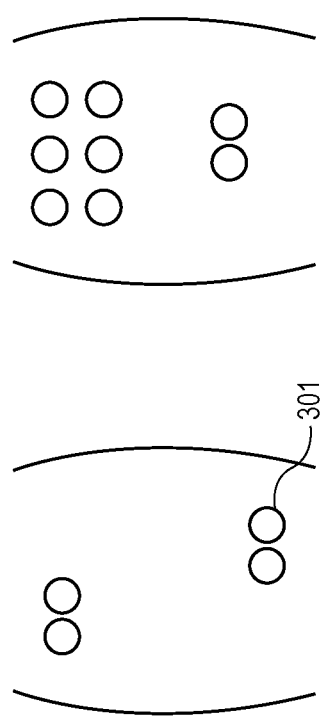

FIG. 2(b) illustrates an exemplary embodiment where a mechanism (205) is implemented to reduce the outward direction lateral spreading of energy. As shown, a greater percentage of energy from the two pairs of electrodes now may combine synergistically. Additionally, even the portion of energy from a given electrode pair that still spreads laterally beyond the region where it can synergistically combine with energy from the other electrode pair will now be more focused in the desired stimulation region than it was without the use of mechanism 205, further improving muscle contraction efficiency. These improvements in efficiency will allow for the original energy amplitude provided by each electrode pair to be reduced without decreasing the degree of muscle contraction achieved, thus reducing current density in superficial regions of tissue and improving comfort. FIG. 2(b) therefore illustrates an exemplary embodiment which overcomes shortcomings of the design shown in FIG. 2(a)

As shown in FIGS. 3(a)-(g), a number of possible arrangements for surface electrodes (301) that may be desirable for use to implement the methods, systems, and devices disclosed in this document. Electrodes may be placed individually or may be combined into a larger structure which I refer to as a stimulation pad (302). The electrode arrangements illustrated in FIGS. 3(a)-(g) are provided by way of example only, and it will be obvious to those skilled in the art that many other electrode arrangements are feasible for use.

FIGS. 4(a)-(c) illustrate methods, devices, and systems to improve comfort during NMES using two or more pairs or groups of electrodes with rapidly switching polarity. FIG. 4(a) provides an overview of the functionality of an exemplary embodiment of the method and systems. A stimulation pad (401) includes two groups of three surface electrodes (402 and 403), labeled 1, 2, and 3 for group 1 and a, b, and c from group 2. In a preferable implementation of the method, an early step involves having electrodes 1 and a simultaneously or near-simultaneously take on positive voltages relative to electrodes 2 and b, respectively, while electrodes 3 and c remain neutral. After a very short period of time, electrodes 1 and a take on a neutral polarity, while electrodes 2 and b become positive relative to electrodes 3 and c, respectively. Without wishing to be bound by any theory, it is believed that when polarity switches are precisely and properly timed, a current field such as that shown in FIG. 4(a) will result. This process may be repeated many times per second to deliver a series of guided stimulation pulses to tissue.

As shown in FIG. 4(b), one implementation of an exemplary system includes a stimulation pad positioned on a body of a user (405), in communication with a control unit via a wired connection. FIG. 4(c) shows four example electrode configurations to be used as part of a system implementing the rapid polarity switching embodiment described herein. These configurations are provided only by way of example, and other similar electrode arrangements will now be obvious to those skilled in the art.

FIGS. 5(a)-(e) illustrate several exemplary embodiments comprising at least one impedance modification element to increase NMES efficiency by reducing lateral energy spreading between pairs or groups of electrodes. The embodiments in FIGS. 5(a)-(e) utilize athermal gradient to increase NMES efficiency by reducing lateral energy spreading between pairs or groups of electrodes. In FIG. 5(a), three pairs of individually-placed stimulation electrodes (501) are placed on a body part, while chemical or gel-based cooling elements (502), which are not integral with one another, are placed laterally in a region adjacent to the electrodes. The cooling elements are positioned laterally on both sides of the electrodes. In FIG. 5(a), the system cooling element comprises two cooling elements 502 that do not extend across an entire width of any of the electrodes. While the cooling element to the left in FIG. 5(a) extends partially across a width dimension of the left electrode without any hash marks, it does not extend across an entire width dimension of the electrode. And while the cooling element to the right in FIG. 5(a) partially extends across a width dimension of one of the electrodes, it does not extend an entire width of the electrode. In FIG. 5(b) two pairs of individually-placed electrodes are separated by a fluid-filled lumen (503) that is continuously infused with a chilled fluid (ex. water, saline) by a pump system (504). In FIG. 5(c), two pairs of electrodes are saddled by two cooling elements (505), shown as pouches containing an ice bath. The cooling element to the right in Figure (c) is positioned solely laterally to both sets of electrodes, while the cooling element on the left is positioned such that is extends partially across a width of one of the sets of electrodes, but is positioned solely laterally to the other set of electrodes. In FIG. 5(d), three groups of stimulation electrodes are integrated into a larger stimulation pad (506) which includes a specialized zone that interfaces with thermoelectric element (507). A control unit (508) controls temperatures in the thermoelectric element. In FIG. 5(e), a stimulation pad comprising stimulation electrodes includes both regions for tissue cooling (509) and tissue warming (510). The cooling elements in FIG. 5(e) are positioned solely laterally to the electrodes and do not extend across a width of any of them. It should be noted that several of the implementations shown in FIG. 5 (for example, 5(b) and 5(d)) would not only limit lateral spreading of electrical energy but may also provide increased penetration of energy to deep-lying muscle tissues.

FIGS. 6(a)-6(d) illustrate various aspects of phase delay timing between multiple electrode channels and provides an example system that implements the timing method described in the specification above. In FIG. 6(a), three electrode pairs (601) are placed and respective stimulation pulses are timed ideally, and maximum energy coordination and synergy at a deep focal point is achieved. In FIG. 6(b), the electrodes are misaligned (for example, an operator places a stimulation pad on in a crooked fashion). Thus, a new phase delay profile between the stimulation pulses delivered by the three electrode pairs is required in order to maintain maximum energy coordination at depth. This illustrates explicitly why a single pre-programmed phase delay is inadequate for optimal performance. As visualized in FIG. 6(c), varying body geometries between users and/or patients will also change the ideal phase delay combination for maximum coordination, further illustrating the need for devices, systems, and methods to optimize phase delays on the per-use basis.

FIG. 6(d) illustrates an exemplary embodiment of a system that implements an adaptive optimization of phase delays between stimulation pulses applied by different pairs or groups of electrodes. Control unit (602) with internal processing and data input/output capabilities is in communication with stimulation pad (603) housing surface stimulation electrodes and with sensor system (604) capable of detecting the relative degree of muscle contraction. This sensor system may be based upon EMG, accelerometers, or other custom sensors known to those skilled in the art. The control unit initiates a sequence of stimulation events using a default series of phase delay profiles. Based upon sensor data resulting from these default stimulation events and custom signal processing, a phase delay profile is selected for use during the NMES treatment session.

Figure 7A:
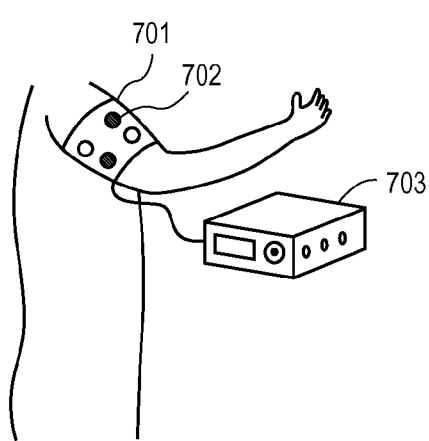
FIGS. 7(a)-(c) illustrate several embodiments where at least two stimulation waveforms are utilized during treatment.
Figure 7B:
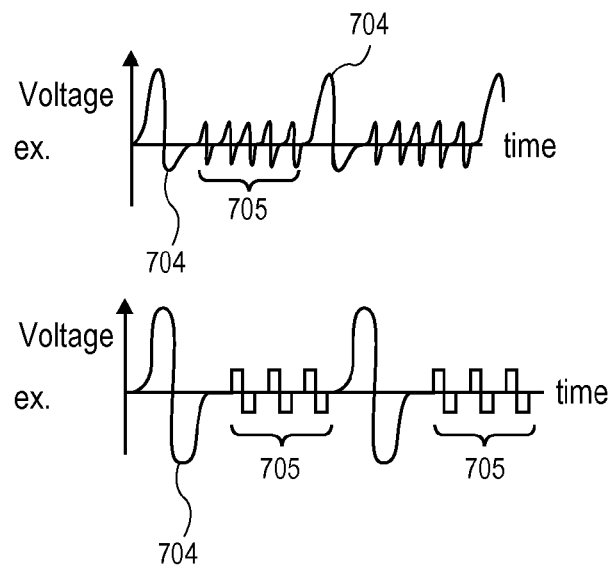
Figure 7C:
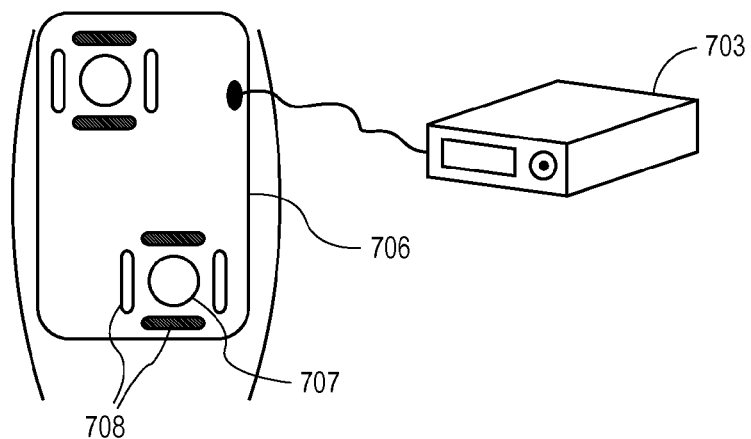

FIGS. 7(a)-(c) illustrate example embodiments of systems, devices, and methods that utilize simultaneous or near-simultaneous delivery of more than one type of energy waveform. In FIG. 7(a), stimulation pad (701) including two pairs of stimulation electrodes (702) is in electrical communication with control unit (703). Each of these electrodes multiplexes an output between both pain-relieving and muscle-stimulation electrical waveforms. By way of example, two preferable multiplexing embodiments are shown in FIG. 7(b). Both embodiments shown contain both muscle-activating (704) pulses and relatively lower-amplitude (but higher repetition frequency) pain-relief pulses (705).

A variation of the embodiment that utilizes more than one type of energy waveform is shown in FIG. 7(c). In this example, separate electrodes are used to deliver pain-relieving and muscle-activating energy. A control unit (703) communicates with a stimulation pad (706) containing both muscle-activating (707) and pain-relief (708) electrodes. By positioning the pain-relief electrodes in specific positions, muscle contraction can be induced with minimal discomfort to the user.

While an impedance modification element is primarily described herein as a cooling element to induce a temperature change in tissue, alternative types of impedance modification elements can be used in place of a cooling element or in conjunction with a cooling element. For example, topical or injected chemical substances may be utilized to create impedance gradients similar to those created with strategically-induced thermal gradients in tissue. For example, an aerosol or similar spray can be applied to skin that temporarily changes its conductive properties. Alternatively, an electric/magnetic/electro-magnetic field generation device that electrically polarizes cells is used to alter their natural conductance. Alternatively, a pressure-generating device can be used to compress cells and/or move excess edematous fluid away from the region of interest.

Additionally, while the devices and methods of use herein are primarily described for muscle stimulation, the devices may be used in other applications. For example, the systems may be used with, for example without limitation, deep brain stimulation, or other targeted stimulation systems where it would be desirable to use a minimal amount of energy.

While preferable embodiments have been shown and described herein, it will be obvious to those skilled in the art that such embodiments are provided by way of example only. Numerous variations, changes, and substitutions will now occur to those skilled in the art without departing from that which is disclosed herein. It should be understood that various alternatives to the embodiments of the disclosure may be employed.

What is claimed is:

1. A system for guiding the flow of energy through a subject to stimulate the contraction of muscle tissue, comprising:
    first and second electrodes adapted to be positioned on the subject and adapted to deliver energy to the subject to stimulate the contraction of muscle tissue;
    a stimulation control unit in communication with the first and second electrodes and configured to generate stimulating energy adapted to stimulate the contraction of muscle tissue and to deliver the stimulating energy to the first and second electrodes; and
    an impedance modification element positioned laterally relative to at least one of the first and second electrodes such that it does not extend across an entire width of at least one of the first and second electrodes, wherein the impedance modification element is adapted to increase the impedance of tissue within the subject to reduce lateral spreading of the energy delivered between the first and second electrodes.

2. The system of claim 1 wherein the impedance modification element comprises a cooling element adapted to decrease the temperature of the tissue within the subject to thereby increase the impedance of the tissue within the subject.

3. The system of claim 1 wherein the impedance modification element is positioned laterally on both sides of the first and second electrodes.

4. The system of claim 3 wherein the impedance modification element does not extend across the widths of either the first or second electrodes.

5. The system of claim 4 wherein the impedance modification element comprises a first impedance modification element positioned on a first side of the first and second electrodes and a second impedance modification element not integral with the first impedance modification element positioned on a second side of the first and second electrodes.

6. The system of claim 1 wherein the impedance modification element is positioned solely laterally to the first and second electrodes.

7. The system of claim 6 wherein the impedance modification element comprises a first impedance modification element positioned solely laterally to the first and second electrodes on a first side of the first and second electrodes and a second impedance modification element not integral with the first impedance modification element positioned solely laterally to the first and second electrodes on a second side of the first and second electrodes.

8. The system of claim 1 further including a housing adapted to be positioned on the subject, wherein the housing houses the first and second electrode.

9. The system of claim 8 wherein the electrodes are pre-established in a stimulation pattern within the housing.

10. The system of claim 8 wherein the housing also comprises the impedance modification element.

11. A system for guiding the flow of energy through a subject to stimulate the contraction of muscle tissue, comprising:
- a first set and a second set of electrodes adapted to be positioned on the subject and adapted to deliver energy to the subject to stimulate the contraction of muscle tissue;
- a stimulation control unit in communication with the first and second sets of electrodes and configured to generate stimulating energy adapted to stimulate the contraction of muscle tissue and to deliver the stimulating energy to the first and second sets of electrodes; and
- an impedance modification element positioned laterally to the first and second sets of electrodes, wherein the impedance modification element is adapted to increase the impedance of tissue within the subject to increase the amount of energy from the first and second sets of electrodes that combines.

12. The system of claim 11 wherein the impedance modification element comprises a cooling element adapted to decrease the temperature of the tissue within the subject to thereby increase the impedance of the tissue within the subject.

13. The system of claim 11 wherein the impedance modification element comprises a first impedance modification element positioned on a first side of the first and second sets of electrodes and a second impedance modification element not integral with the first impedance modification element positioned on a second side of the first and second sets of electrodes.

14. The system of claim 11 wherein the impedance modification element is positioned solely laterally to the first and second sets of electrodes.

15. The system of claim 14 wherein the impedance modification element comprises a first impedance modification element positioned solely laterally to a first side of the first and second sets of electrodes and a second impedance modification element not integral with the first impedance modification element positioned solely laterally to a second side of the first and second sets of electrodes.

16. The system of claim 11 further including a housing adapted to be positioned on the subject, wherein the housing comprises the first and second sets of electrodes.

17. The system of claim 16 wherein the sets of electrodes are pre-established in a stimulation pattern within the housing.

18. The system of claim 16 wherein the housing also comprises the impedance modification element.

* * * * *